United States Patent
Flohr et al.

(10) Patent No.: US 8,897,531 B2
(45) Date of Patent: Nov. 25, 2014

(54) METHOD AND COMPUTED TOMOGRAPHY SYSTEM FOR GENERATING TOMOGRAPHIC IMAGE DATASETS WITH INTEGRATING DETECTOR AND COUNTING DETECTOR

(75) Inventors: Thomas Flohr, Uehlfeld (DE); Gabriel Haras, Mücke (DE); Daniel Niederlöhner, Erlangen (DE); Stefan Pflaum, Hirschaid (DE)

(73) Assignee: Siemens Aktiengesellschaft, Munich (DE)

(*) Notice: Subject to any disclaimer, the term of this patent is extended or adjusted under 35 U.S.C. 154(b) by 219 days.

(21) Appl. No.: 13/478,502

(22) Filed: May 23, 2012

(65) Prior Publication Data
US 2012/0301001 A1 Nov. 29, 2012

(30) Foreign Application Priority Data
May 24, 2011 (DE) .......................... 10 2011 076 348

(51) Int. Cl.
G06K 9/00 (2006.01)
A61B 6/00 (2006.01)
A61B 6/03 (2006.01)
G06T 11/00 (2006.01)

(52) U.S. Cl.
CPC ............. *A61B 6/4241* (2013.01); *A61B 6/5235* (2013.01); *A61B 6/032* (2013.01); *G06T 11/006* (2013.01); *A61B 6/503* (2013.01); *A61B 6/482* (2013.01); *G06T 2211/412* (2013.01)
USPC ........................................................ 382/131

(58) Field of Classification Search
None
See application file for complete search history.

(56) References Cited

U.S. PATENT DOCUMENTS

| | | | | |
|---|---|---|---|---|
| 5,848,117 A | * | 12/1998 | Urchuk et al. | 378/19 |
| 7,424,088 B2 | * | 9/2008 | Zamyatin et al. | 378/4 |
| 2006/0067457 A1 | * | 3/2006 | Zamyatin et al. | 378/4 |
| 2007/0121779 A1 | * | 5/2007 | Nishide et al. | 378/4 |
| 2007/0205367 A1 | * | 9/2007 | Deman et al. | 250/363.02 |
| 2008/0144765 A1 | * | 6/2008 | Flohr | 378/9 |
| 2010/0195787 A1 | * | 8/2010 | Flohr et al. | 378/8 |
| 2010/0278296 A1 | * | 11/2010 | Edic et al. | 378/5 |
| 2011/0085637 A1 | * | 4/2011 | Boese et al. | 378/4 |

(Continued)

FOREIGN PATENT DOCUMENTS

DE 102006007058 A1 7/2007

OTHER PUBLICATIONS

German Office Action for German Application No. 10 2011 076 348.1, Feb. 1, 2012.

(Continued)

*Primary Examiner* — Tahmina Ansari
(74) *Attorney, Agent, or Firm* — Harness, Dickey & Pierce, P.L.C.

(57) ABSTRACT

A method and a dual-source CT are disclosed. In at least one embodiment, the projection data of the integrating and of the counting detector from a quarter rotation of the gantry is used jointly for reconstruction of a first tomographic image dataset, the energy-resolved projection data of the counting detector from at least one half rotation of the gantry being used for reconstruction of at least a second material-selective tomographic image dataset, and at least one tomographic result image dataset being formed by overlaying the first tomographic image dataset with the material selection of the second image dataset.

15 Claims, 2 Drawing Sheets

(56) References Cited

U.S. PATENT DOCUMENTS

2011/0255657 A1* 10/2011 Noordhoek ..................... 378/11
2012/0014582 A1* 1/2012 Schaefer et al. .............. 382/131
2012/0301001 A1* 11/2012 Flohr et al. ................... 382/131
2013/0077847 A1* 3/2013 Hansis et al. ................. 382/131
2013/0108013 A1* 5/2013 Leng et al. ..................... 378/19

OTHER PUBLICATIONS

German Priority Document DE 10 2011 076 348.1 filed May 24, 2011 (not yet published).
Chinese Office Action issued in Chinese Patent Application No. 2012101644505, dated Apr. 23, 2014, and English translation.

* cited by examiner

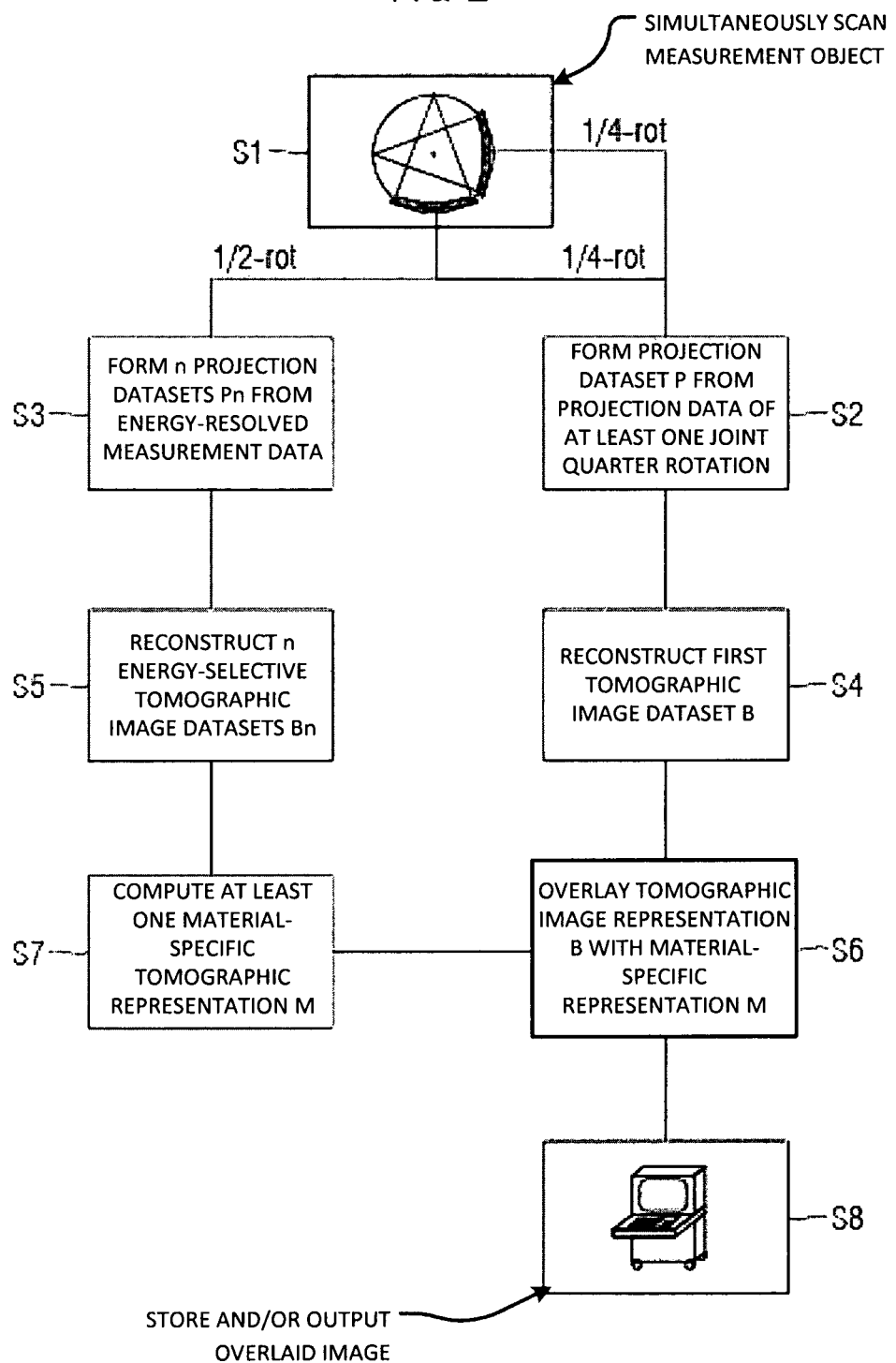

METHOD AND COMPUTED TOMOGRAPHY SYSTEM FOR GENERATING TOMOGRAPHIC IMAGE DATASETS WITH INTEGRATING DETECTOR AND COUNTING DETECTOR

PRIORITY STATEMENT

The present application hereby claims priority under 35 U.S.C. §119 to German patent application number DE 10 2011 076 348.1 filed May 24, 2011, the entire contents of which are hereby incorporated herein by reference.

FIELD

At least one embodiment of the invention generally relates to a method and/or a computed tomography system for generating tomographic image datasets of an at least cyclically moving part of a measurement object, especially a heart of a patient, with the aid of a dual-source CT system with two detectors disposed offset at an angle to each other on a gantry, with an integrating detector measuring incident radiation integrationally over the entire energy spectrum of the incident radiation, and simultaneously a counting detector measuring incident radiation by way of resolution in at least two energy ranges.

BACKGROUND

Dual-source CT systems with a conventional integrating scintillation detector and a counting detector are known. In such cases both measurement systems are operated simultaneously to scan a measurement object, mostly a patient. Such a dual-source CT system contains two emitter-detector systems including an x-ray emitter and the respectively associated detector in each case, which are disposed offset at an angle to each other on a gantry.

SUMMARY

A problem here is that of reconstructing readily recognizable tomographic image data when the measurement object moves, with information relating to the material properties of the measurement object also having to be displayed at the same time.

An embodiment of the invention is directed to a method and/or a computed tomography system for generating tomographic image datasets of an at least cyclically moving part of a measurement object, especially the heart of a patient, with the aid of a dual-source CT system, which method and computed tomography system on the one hand allow temporally highly resolved image data to be obtained and on the other hand also enable information relating to the presence of specific materials such as contrast agent or plaque to be recognized in this image data.

Advantageous embodiments of the invention are the subject matter of subordinate claims.

This method of at least one embodiment comprises:
using the projection data of the integrating and of the counting detector from a quarter revolution of the gantry jointly for reconstruction of a first tomographic image dataset,
using the energy-resolved projection data of the counting detector from at least one half revolution of the gantry for reconstruction of at least one second material-selective tomographic image dataset, and
forming at least one tomographic result image dataset for overlaying the first tomographic image dataset with the material selection of the second image dataset.

A dual-source CT system of at least one embodiment comprises:
two detectors able to be operated simultaneously for simultaneous offset-angle scanning of a measurement object from a multiplicity of projection angles, with
a first detector being designed for integrational x-ray measurement and
a second detector being designed to resolve an incident radiation spectrum into at least two energy bins, and
a computer system for evaluation of measurement results of the detector elements, said computer system having a memory and computer programs located therein,
with there also being present in the memory of the computer system at least one computer program which executes the above-described method during operation.

BRIEF DESCRIPTION OF THE DRAWINGS

The invention is described below with the aid of the figures, with only the features necessary for understanding the invention being presented. The following reference characters are used: 1: CT system; 2: first x-ray tube; 3: first detector; 4: second x-ray tube; 5: second detector; 6: gantry housing; 7: patient; 8: patient couch; 9: system axis; 10: computer system; 11: contrast agent applicator; 12: ECG line; B: first tomographic image dataset; Bn: second material-selective tomographic image dataset; BM: second tomographic result image dataset; M: second tomographic image dataset; P: projection data of the counting and integrating detector from a ¼ revolution; Pn: energy-resolved projection data; Prg1-Prgn: computer programs; ½-rot: half rotation; ¼-rot: quarter rotation; S1-S8: method steps.

The individual figures are as follows:
FIG. 2: Schematic execution sequence of an embodiment of the method.

Figure 1:
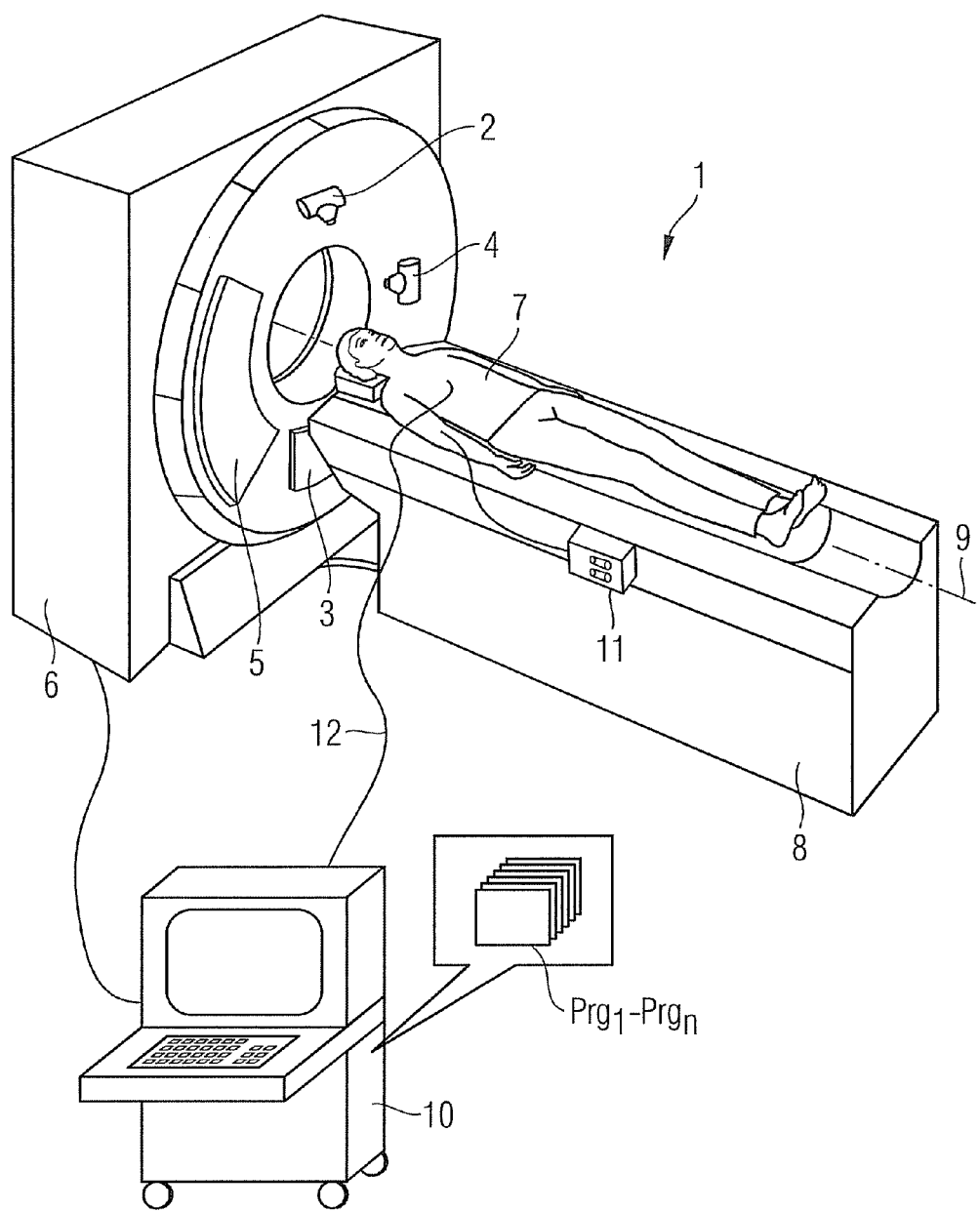
FIG. 1: CT system for carrying out an embodiment of the inventive method.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The inventors have recognized the following:

Computed tomography (CT) devices used in medicine today are equipped with integrating scintillation detectors as the prior art. In them, the incident x-rays are initially converted in a two-stage process into visible light which is then detected by downstream photodiodes and transformed into electrical signals. Examples of appropriate scintillators are gadolinium oxide or gadolinium oxide sulfide. Such scintillating detectors have a very wide dynamic range and can easily process the minimum and maximum x-ray flux densities used in medical computed tomography.

On the other hand their spatial resolution is limited, since for mechanical reasons the detector pixels cannot be reduced in size at will for purposes of mechanical and optical separation due to inactive dead zones between the pixels.

In addition integrating scintillation detectors do not supply any spectral information, so that material characteristic differences in x-ray absorption at different energies of the x-ray spectrum cannot be detected directly. Furthermore the contrast-to-noise ratio of the detected signals from integrating detectors is not optimal since the low energy quanta which carry the most contrast information are also only given a low weighting in the integrating detector in accordance with their low energy, so that the contrast of specific materials, such as white and gray brain matter for example, will be greatly reduced.

By contrast there are counting detectors in which the incident x-ray quanta are converted in a direct process into electrical signals and counted. Examples of corresponding detector materials are cadmium telluride or cadmium zinc telluride. Counting detectors can have a very fine structure on their surface since the pixels do not have to be mechanically separated and therefore there are no dead zones. Thus a significantly higher spatial resolution is possible than with conventional integrating scintillation detectors. In addition the incident x-ray quanta can be detected for a spectral resolution in different energy bands, as a result of which material characteristic differences in x-ray absorption at different energies can be registered with a single measurement. The option of energy-dependent weighting of the contributions to the overall signal also allows the object contrast and thereby the contrast-to-noise ratio to be improved by comparison with integrating scintillation detectors.

A disadvantage of counting detectors however is the limited dynamic range as a result of the detector materials used, in which a maximum x-ray flux density may not be exceeded, which in the current prior art is not high enough for unrestricted use in a medical CT system. A further disadvantage is the high drift of the signals of a counting detector after a previous irradiation, with under some circumstances artifacts which are difficult to correct being produced in the images.

The inventors, in at least one embodiment, have now seen that it is possible, with a combination of projection data from an integrating and a counting detector, to use at least the potentially higher spatial resolution of the counting detector for an overall better image resolution of a tomographic image, through the combination of the measurement data of two simultaneously scanning detectors offset at an angle to each other to improve the temporal resolution compared to scanning with only one detector, and by using the energy resolution to obtain selective material information which can be reproduced combined with a temporally and a spatially highly resolved presentation.

Accordingly the inventors, in at least one embodiment, propose the improvement of a method known per se for generating tomographic image datasets of an at least cyclically moving part of a measurement object, especially a heart of a patient, with the aid of a dual-source CT system with two detectors disposed offset at an angle to each other on a gantry, with an integrating detector integrationally measuring incident radiation over the entire energy spectrum of the incident radiation, and simultaneously a counting detector measuring incident radiation in at least two energy ranges by way of resolution.

This method is improved according to at least one embodiment of the invention in that at least:

the projection data of the integrating and of the counting detector from a quarter revolution of the gantry are used jointly for reconstruction of a first tomographic image dataset, the energy-resolved projection data of the counting detector from at least one half revolution of the gantry are used for reconstruction of at least one second material-selective tomographic image dataset, and at least one tomographic result image dataset is formed for overlaying the first tomographic image dataset with the material selection of the second image dataset.

Advantageously the overlaying of image datasets can be accomplished in that the first at least temporally more highly resolved image dataset is represented as a black-and-white image and a material-selective coloration is carried out using the second, at least temporally less highly resolved image dataset.

It is also worthwhile here for a detector with a higher spatial resolution than the integrating detector to be used as the counting detector.

Finally trigger signals of the cyclic movement of the measurement object can be recorded additionally and the measurement data of the counting and/or integrating detector from at least two movement cycles can be combined.

As well as the inventive method, a dual-source CT system of at least one embodiment is also proposed comprising:

two detectors able to be operated simultaneously for simultaneous offset-angle scanning of a measurement object from a multiplicity of projection angles, with a first detector being designed for integrational x-ray measurement and a second detector being designed to resolve an incident radiation spectrum into at least two energy bins, and a computer system for evaluation of measurement results of the detector elements, said computer system having a memory and computer programs located therein, with there also being present in the memory of the computer system at least one computer program which executes the above-described method during operation.

FIG. 1 shows an example of a CT system 1 with two emitter-detector systems on a gantry, which is not shown in any greater detail, in a gantry housing 6. The two emitter-detector systems, consisting of a first x-ray tube 2, with a first detector 3 associated with the first x-ray tube arranged opposite the tube with integrating detector elements and the second x-ray tube 4, with a second detector 5 associated with the second x-ray tube arranged opposite said tube with counting detector elements, are disposed here on a gantry not shown in any greater detail offset by an angle of 90° in a plane of rotation.

Both emitter-detector systems 2, 3 and 4, 5 scan a field of view located in the central circular bore. A measurement object, especially a patient 7 as shown here, can be moved through this field of view with the aid of the patient couch 8 along the system axis 9. Basically both a spiral scan and also a sequential scan can be carried out with this arrangement. For improving the imaging of blood vessels or other structures a contrast agent can also be injected into the patient by means of the contrast agent applicator 11. Heart actions can also be scanned via the ECG line 12 in order to carry out a heart-action-triggered scanning and/or reconstruction.

The CT system 1 is controlled and the scan of the patient 7 evaluated by the computer system 10 connected to the CT system, with the computer system having at least one memory in which computer programs Prg1-Prgn are stored. According to an embodiment of the invention, programs are also contained or stored in the memory, which programs are embodied to execute the different embodiments of the inventive method during operation of the system.

A typical execution of an embodiment of the inventive method is shown schematically in FIG. 2. In accordance with this diagram, first of all, in method step S1, a simultaneous scan of the measurement object with the integrating and the counting detector over an angle of rotation of at least 180°+ fan angle of the larger of the two detectors corresponding to a half rotation is carried out and the projection data determined in this step is stored.

From the projection data of the at least one joint quarter rotation of the two detectors contained in the half rotation a first projection dataset P is then formed in which both the integrated measured projection data of the first detector over a quarter rotation and also the energy-resolved projection data of the second detector is contained summed over all energies (step S2). Subsequently, in step S4, a first temporally highly resolved, tomographic image dataset B is reconstructed from this first projection dataset.

In parallel with this, in step S3, n second projection datasets PN are formed from the energy-resolved measurement data of the second counting detector in accordance with the present energy resolution into n energy ranges, and n energy-selective tomographic image datasets Bn are reconstructed with these in step S5. Subsequently, in step S7, at least one material-specific tomographic representation M is computed with the aid of the energy-selective image datasets.

Finally the high-resolution tomographic image representation B is overlaid with the material-specific but lower-resolution, graphic presentation M. This can be done for example by the percentage presence of individual materials being represented by percentage color components of a color mixture in the material-specific representation M and this coloration being overlaid, in step S6, transparently onto the black-and-white high-resolution image presentation B to form a material-specific colored image composition BM and stored for subsequent presentation or in step S8 output directly on a monitor.

Overall embodiment of the invention thus proposes a method and/or a dual-source CT system for generating tomographic image datasets of an at least cyclically moving part of a measurement object, with two detectors disposed offset at an angle to each other on a gantry, with one integrating detector measuring over the entire energy spectrum and simultaneously a counting detector measuring in a resolving manner in at least two energy ranges. In this case a first image dataset is formed from projection data of the integrating and the counting detector from one quarter rotation in each case and a second material-selective tomographic image dataset is generated from energy-resolved projection data of the counting detector from at least one half rotation, and at least one tomographic result image dataset is formed by overlaying the first image dataset with the material-selective second image dataset.

Although the invention has been illustrated and described in detail by means of the preferred exemplary embodiments, the invention is not restricted by the disclosed examples and other variations can be derived therefrom by the person skilled in the art without departing from the scope of protection of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating a tomographic result image dataset of an at least cyclically moving part of a measurement object, with the aid of a dual-source CT system including two detectors on a gantry, the two detectors being offset at an angle to each other, the two detectors including an integrating detector to integrationally measure incident radiation over an entire energy spectrum of the incident radiation, and a counting detector to simultaneously measure incident radiation in at least two energy ranges in a resolving manner, the method comprising:
   using projection data of the integrating and the counting detector from a quarter rotation of the gantry jointly, for reconstruction of a first tomographic image dataset;
   using energy-resolved projection data of the counting detector from at least one half rotation of the gantry for reconstruction of at least one second material-selective tomographic image dataset; and
   forming at least one tomographic result image dataset by overlaying the reconstructed first tomographic image dataset with the reconstructed second material-selective tomographic image dataset.

2. The method of claim 1, wherein the overlaying of the image datasets comprises:
   representing a first resolved image dataset as a black-and-white image; and
   carrying out a material-selective coloration using a second resolved image dataset, the first resolved image dataset being at least temporally more highly resolved than the second resolved image dataset.

3. The method of claim 1, wherein the counting detector has a higher spatial resolution than the integrating detector.

4. The method of claim 1, further comprising:
   recording trigger signals of cyclic movement of the measurement object; and
   combining the measurement data of at least one of the counting and integrating detectors from at least two movement cycles.

5. A dual-source CT system, comprising:
   a plurality of detectors simultaneously operable for simultaneous angle-offset scanning of a measurement object from a multiplicity of projection angles, a first of the plurality of detectors being an integrating detector configured to perform integrational radiation measurement, and a second of the plurality of detectors being a counting detector configured to resolve an incident radiation spectrum into at least two energy bins; and
   a computer system to evaluate measurement results of elements of the plurality of detectors, said computer system including a memory with computer programs located therein, at least one of the computer programs, when executed, causes the computer system to,
      use projection data of the integrating and the counting detector from a quarter rotation of the gantry jointly, for reconstruction of a first tomographic image dataset,
      use energy-resolved projection data of the counting detector from at least one half rotation of the gantry for reconstruction of at least one second material-selective tomographic image dataset, and
      form at least one tomographic result image dataset by overlaying the reconstructed first tomographic image dataset with the reconstructed second material-selective tomographic image dataset.

6. The method of claim 2, wherein the counting detector has a higher spatial resolution than the integrating detector.

7. The method of claim 2, further comprising:
   recording trigger signals of cyclic movement of the measurement objects and
   combining the measurement data of at least one of the counting and integrating detectors from at least two movement cycles.

8. The method of claim 3, further comprising:
   recording trigger signals of cyclic movement of the measurement object; and
   combining the measurement data of at least one of the counting and integrating detectors from at least two movement cycles.

9. The method of claim 1, wherein the measurement object is a heart of a patient.

10. A non-transitory computer readable medium including program segments that, when executed on a computer device, cause the computer device to implement the method of claim 1.

11. The non-transitory computer readable medium of claim 10, wherein the method further comprises:

recording trigger signals of cyclic movement of the measurement object; and combining the measurement data of at least one of the counting and integrating detectors from at least two movement cycles.

12. The dual-source CT system of claim 5, wherein the counting detector has a higher spatial resolution than the integrating detector.

13. The dual-source CT system of claim 12, wherein at least one of the computer programs, when executed, causes the computer system to:

record trigger signals of cyclic movement of the measurement object; and combine the measurement results of at least one of the counting and integrating detectors from at least two movement cycles.

14. The dual-source CT system of claim 5, wherein at least one of the computer programs, when executed, causes the computer system to:

record trigger signals of cyclic movement of the measurement object; and combine the measurement results of at least one of the counting and integrating detectors from at least two movement cycles.

15. The dual-source CT system of claim 5, wherein the measurement object is a heart of a patient.

* * * * *